United States Patent
Robinson et al.

(10) Patent No.: US 8,450,554 B2
(45) Date of Patent: May 28, 2013

(54) SYSTEM AND METHOD FOR HEALING A WOUND AT A TISSUE SITE

(75) Inventors: Timothy Mark Robinson, Basingstoke (GB); Kristine Kiesweller, San Antonio, TX (US); Amy McNulty, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 446 days.

(21) Appl. No.: 12/394,618

(22) Filed: Feb. 27, 2009

(65) Prior Publication Data

US 2009/0216170 A1    Aug. 27, 2009

Related U.S. Application Data

(60) Provisional application No. 61/032,014, filed on Feb. 27, 2008.

(51) Int. Cl.
*A61F 13/00*    (2006.01)

(52) U.S. Cl.
USPC .............. 602/54; 602/41; 602/42; 156/712; 156/753; 604/304

(58) Field of Classification Search
USPC ............. 602/48–52, 54–57; 604/304–308; 424/443–449; 156/712, 753, 711, 703, 704
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Patricia Bianco
*Assistant Examiner* — Kari Petrik

(57) ABSTRACT

Provided herein is a system and method for facilitating removal of a drape from a tissue site. One aspect provides a system comprising a drape, and adhesive layer, and a release agent, where the system is adapted to be coupled to a tissue site and released therefrom upon or after exposure to an external stimulus. Another aspect provides a method for application and removal of a drape using less force than required with a conventional drape.

7 Claims, 5 Drawing Sheets

U.S. PATENT DOCUMENTS

| | | | |
|---|---|---|---|
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,140,115 A | 2/1979 | Schonfeld | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,921,757 A * | 5/1990 | Wheatley et al. | 428/402.2 |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,032,637 A | 7/1991 | Therriault et al. | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,156,911 A | 10/1992 | Stewart | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,397,614 A | 3/1995 | Patnode et al. | |
| 5,412,035 A | 5/1995 | Schmitt et al. | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,679,773 A | 10/1997 | Holmes | |
| 5,947,917 A * | 9/1999 | Carte et al. | 602/52 |
| 6,071,267 A | 6/2000 | Zamierowski | |
| 6,084,010 A | 7/2000 | Baetzold et al. | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,432,428 B1 * | 8/2002 | Arquette et al. | 424/401 |
| 6,471,968 B1 | 10/2002 | Baker, Jr. et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,589,736 B1 | 7/2003 | Rothschild et al. | |
| 6,610,762 B1 | 8/2003 | Webster | |
| 6,814,079 B2 | 11/2004 | Heaton et al. | |
| 6,849,462 B1 | 2/2005 | Winkler et al. | |
| 6,946,177 B2 | 9/2005 | Abe et al. | |
| 7,396,976 B2 * | 7/2008 | Hurwitz et al. | 602/58 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0060380 A1 | 3/2003 | Ayarza et al. | |
| 2004/0253281 A1 * | 12/2004 | Herweck et al. | 424/401 |
| 2004/0261943 A1 | 12/2004 | Fukuoka et al. | |
| 2007/0062643 A1 | 3/2007 | Watanabe | |
| 2007/0224378 A1 * | 9/2007 | Takeuchi et al. | 428/40.1 |
| 2007/0249981 A1 | 10/2007 | Hurwitz et al. | |
| 2009/0114344 A1 * | 5/2009 | Barinov et al. | 156/344 |

FOREIGN PATENT DOCUMENTS

| | | |
|---|---|---|
| AU | 755496 | 2/2002 |
| CA | 2005436 | 6/1990 |
| DE | 17 69 580 A1 | 10/1971 |
| DE | 26 40 413 A1 | 3/1978 |
| DE | 43 06 478 A1 | 9/1994 |
| DE | 295 04 378 U1 | 10/1995 |
| EP | 0 080 008 A | 6/1983 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 554 106 A | 8/1993 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| GB | 2 353 219 A | 2/2001 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 92/13901 A | 8/1992 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2006/050340 A | 5/2006 |

OTHER PUBLICATIONS

Louis C. Argenta, MD and Michael J. Morykwas, PhD; "Vacuum-Assisted Closure: A New Method for Wound Control and Treatment:

Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bidirectional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 pages English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," Chronic Wound Care, edited by D. Krasner (Health Management Publications, Inc., King of Prussia, PA 1990), pp. 240-246.
G. Živadinović, V. Đukić, Ž. Maksimović, Đ. Radak, and P. Peška, "Vacuum Therapy in the Treatment of Peripheral Blood Vessels," Timok Medical Journal 11 (1986), pp. 161-164
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and. Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
International Search Report and Written Opinion date mailed Sep. 9, 2009; PCT International Application No. PCT/US2009/035524.
Lin S-Y et al: "Design and evaluation of drug-loaded wound dressing having thermoresponsive, adhesive, absorptive and easy peeling properties" Biomaterials, Elsevier Science Publishers BV., Barking, GB, vol. 22, No. 22, Nov. 15, 2001, pp. 2999-3004, XP004301378, ISSN: 0142-9612.

* cited by examiner

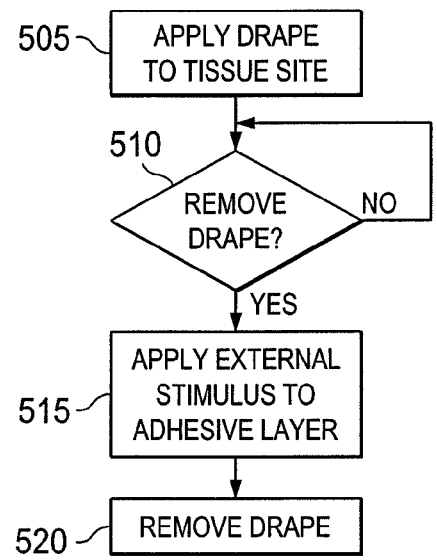
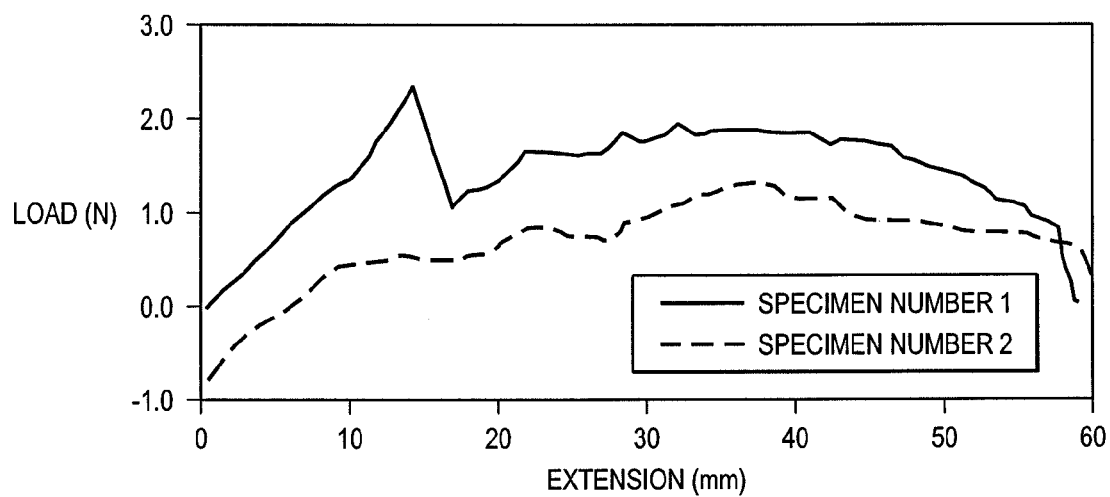

SYSTEM AND METHOD FOR HEALING A WOUND AT A TISSUE SITE

CROSS-REFERENCE TO RELATED APPLICATIONS

This application claims priority from U.S. Provisional Application Ser. No. 61/032,014, filed on Feb. 27, 2008, which is incorporated herein by reference in its entirety.

FIELD OF THE INVENTION

The present application relates generally to the field of tissue treatment, and more specifically to a system and method for facilitating the application and removal of a drape from a tissue site.

BACKGROUND OF THE INVENTION

Systems and devices currently exist for the treatment of tissue, such as wound tissue and skin tissue. Some current tissue treatment systems require the use of an adhesive drape to secure all or a portion of the tissue treatment system to a tissue site. For example, an adhesive drape can be used to secure a gauze portion of a bandage to a wound site by adhering to the skin or other tissue surrounding the wound.

However, when using drapes in current treatment systems, the act of removing the drape can result in pain or discomfort to the patient. This pain or discomfort can be due to continued adhesion between the drape and the tissue site, including the surrounding skin, at the time at which the drape is removed, thereby resulting in stress being applied to the skin or other tissue at the tissue site. This problem is compounded when the tissue site upon which the drape is adhered is friable or fragile. In this circumstance, the removal of current drape can result in damage to the tissue site.

In some instances, a drape adhesive that is more adherent can be desirable during some treatment types in which high shear, high fluid, or high moisture is present at the tissue site. However, such drape adhesive can also lead to patient discomfort when the drape is removed. Thus, a need exists for a drape that secures all or a portion of a tissue treatment system to the tissue site, yet causes less pain and discomfort to a patient when the drape is removed. This need also exists when a drape securing a portion of a reduced pressure treatment system, such as a dressing or manifold, needs to be removed.

SUMMARY OF THE INVENTION

To alleviate the existing problems with reduced pressure treatment systems, the illustrative embodiments described herein are directed to a system and method for facilitating removal of a drape from a tissue site.

One aspect provides a system for healing a wound at a tissue site. The system comprises a drape, an adhesive, and a release agent. The drape is adapted to cover the wound at the tissue site. The adhesive has one surface affixed to at least a portion of the drape and an opposite surface adapted to bond to the tissue site. The release agent is contained within said adhesive and responsive to an external stimulus that weakens the bond of said adhesive to the tissue site. Weakening of the adhesive bond facilitates the removal of said drape from the tissue site.

In some embodiments, the external stimulus comprises at least one of electromagnetic energy; magnetic field; sound; pH level; pressure; thermal energy; moisture; and a stimulus substance. In some embodiments, the system also comprising an adhesive support layer detachably coupled to the adhesive layer. In some embodiments, the amount of force required to remove said drape from the tissue site is decreased by at least about 20% of the amount of force required to remove said drape without said release agent.

In some embodiments, the release agent comprises at least one of a release material and a linker material.

In some embodiments, the release material comprises at least one of: a sub-ambient Tg material; a photopolymer; a natural oil; a synthetic oil; a surfactant; a silicone particle; a paraffin particle; a fluorocarbon particle; a terpene; a solvent; a lipid; a thermally degrading adhesive; a Gecko mimics; an ultrasonic degraded compound; a thermally reversible adhesive; a mussel adhesive protein; a polymer brush; a solvent induced switching; a MEMS device; or a silicone gel. In some embodiments, the release material comprises at least one of: vitamin E; glycerin; glycerol; olive oil; safflower oil; sesame oil; tea tree oil; stearic acid; glycery stearate; retinyl palmitate; allantoin; a soy esters; limonene; DMSO; IPA; ethyl acetate; polyethylene glycol; tetrahydrofurfuryl acetate; trilaurin; a polyvinylsiloxane microscale pillar; a carbon nanotube; a coated PDMS micropattern; a rippled PDMS film; alkoxylate acrylate; PS; PVP; MEMS device; nitrogen; helium; hydrogen; carbon dioxide; oxygen; active oxygen; carbon dioxide; tartaric acid; bicarbonate; calcium carbonate; citric acid; a chlorofluorocarbon; or a hydrocarbon.

In some embodiments, the release material comprises a plurality of gas particles. The gas particles are generated by a reaction between at least two substances in the adhesive layer. The reaction occurs in the presence of the external stimulus. In some configurations, the plurality of gas particles, when released on exposure to the external stimulus, causes an increase in porosity in the adhesive layer that decreases the amount of force sufficient to remove the drape from a tissue site.

In some embodiments, the release material comprises a plurality of oil particles. The oil particles are released on exposure to the external stimulus, weakening a bond between the adhesive layer and the drape or a tissue site or the linker material and the drape, adhesive layer, or a tissue site. The weakened bond decreases the amount of force sufficient to remove the drape from a tissue site.

In some embodiments, the system further comprises a plurality of microstructures for containing said release agent and responsive to the external stimulus to release at least a portion of the release agent. In some embodiments, the plurality of microstructures comprise at least one of: a polymeric delivery system, a microsphere, a polymeric hydrogel, a liposome, or a micelle. In some embodiments, the plurality of microstructures comprise at least one of: a polysachharide; N-acetyl-glcosamine; silicone; latex; poly-lactide-co-glycolide; poly-ethylene vinyl-co-acetate; a polyanhydride; polyvinyl alcohol; polyphosphazene; PLA; PLGA; PLGA coated with DPPC, DPPC, DSPC, or EVAc; gelatin; albumin; chitosan; dextran; cyclodextran; DL-PLG SDLMs; PEG; sodium hyaluronate; a diketopiperazine derivative; a calcium phosphate-PEG particle; an oligosaccharide derivative; a phospholipid; sodium dodecyl sulfate; dodecyl maltoside; collagen; fibrin; alginate; a polyalkylacrylic acid polymer; casein; lecithin; phosphatidylcholine; phosphatidylethanolamine; sphingomyelin; phosphatidylserine; phosphatidylglycerol; phosphatidylinositol; a ceramic; or glass; or a combination or polymer thereof.

In some embodiments, the linker material comprises at least one of: a benzoin derivative; a photolabile linker; a light reversible polymer; a thermo-responsive polymer; a shape memory polymer; a pH sensitive polymer; an analyte sensitive polymer; or a photocrosslinker. In some embodiments, the linker material comprises at least one of: dimethoxybenzoin; dimethylproprionic acid; 3,5-dimethoxybenzyl acetate; 4-(2-chloroproprionyl)phenyl acetic acid; poly(N-isopropylacrylamide); poly(ethylene oxide); poly(propylene oxide); poly(N,N'-methylenebisacrylamide); oligo($\epsilon$-caprolactone) dimethylacrylate; poly(methacrylic acids); phospholipids; a silicon-based polysilamine gel; disialyllacto-N-tetraose; and a dental composite.

In some embodiments, the drape is coupled to the adhesive layer, the adhesive layer is coupled to the linker material, and the linker material is adapted to couple to a tissue site. In some embodiments, the drape is coupled to the adhesive layer, the adhesive layer is coupled to the linker material, and the linker material is adapted to couple to a tissue site. In some embodiments, the adhesive layer comprises a first adhesive layer and a second adhesive layer; the drape is coupled to the first adhesive layer; the first adhesive layer adhesive layer is coupled to the linker material; linker material is coupled to the second adhesive layer; and the second adhesive layer is adapted to couple to a tissue site. In some embodiments, the adhesive layer comprises a first adhesive layer and a second adhesive layer; the drape is coupled to the first adhesive layer; the first adhesive layer adhesive layer is coupled to the linker material; linker material is coupled to the second adhesive layer; and the second adhesive layer is adapted to couple to a tissue site. In some embodiments, the microstructures are coupled to the linker material and the linker material is coupled to the adhesive layer.

In some embodiments, the linker material is coupled to said drape via an electrostatic force. In some embodiments, the linker material is coupled to said adhesive layer via an electrostatic force. In some embodiments, the linker material is coupled to said plurality of microstructures via an electrostatic force. In some embodiments, the linker material is adaptable to be coupled to the tissue site via an electrostatic force.

Another aspect provides a kit for healing a wound at a tissue site. In some embodiments, the kit comprises a system as described above. In some embodiments, the kit comprises each component of a system described above packaged together or separately and adapated to be combined prior to application to a tissue site. In some embodiments, the kit further comprises one or more of a dressing, a drape, manifold, adhesive, adhesive backing, adhesive tape, a release agent, a release material, a linker material, a microstructure, an external stimulus agent, an external stimulus source, an external energy source, an antiseptic swab, and a skin preparation swab. In some embodiments, the kit further comprises instructions for the application or removal of the system or components thereof.

Another aspect provides a method for facilitating removal of a drape from a tissue site. The method comprises adhering a system as described above. The method comprises exposing the system to an effective amount of an external stimulus sufficient to release the release agent so as to decrease an amount of force sufficient to remove the system from the tissue site. In some embodiments, the method comprises removing at least the drape from the tissue site. In some embodiments, the method comprises removing at least the drape and a substantial portion of the adhesive layer from the tissue site.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 5 is a flowchart illustrating a process for facilitating removal of a drape 125 from a tissue site 105 in accordance with an illustrative embodiment of the present invention; and FIG. 6 is a line plot showing load (N) as a function of extension (mm) for specimen 1 and specimen 2. Further details regarding methodology are provided in Example 1.

DETAILED DESCRIPTION OF THE PRESENTLY PREFERRED EMBODIMENTS

Figure 1A:
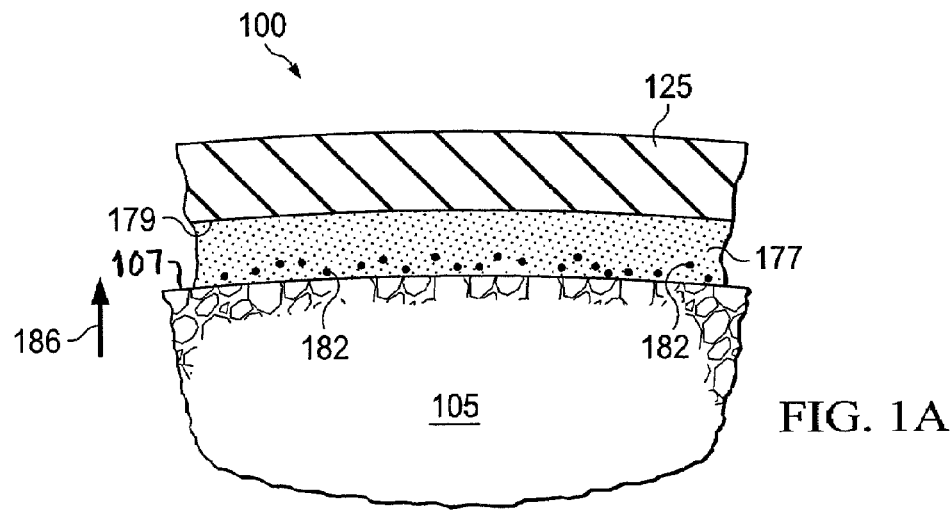
FIG. 1A is a cross-sectional view of a system for facilitating removal of a drape 125 from a tissue site 105 in accordance with an illustrative embodiment of the present invention.

In the following detailed description of the preferred embodiments, reference is made to the accompanying drawings that form a part hereof, and in which is shown by way of illustration specific preferred embodiments in which the invention can be practiced. These embodiments are described in sufficient detail to enable those skilled in the art to practice the invention, and it is understood that other embodiments can be utilized and that logical structural, mechanical, electrical, and chemical changes can be made without departing from the spirit or scope of the invention. To avoid detail not necessary to enable those skilled in the art to practice the invention, the description can omit certain information known to those skilled in the art. It is understood that reference to a feature by numeric designation does not necessarily refer only to any particular embodiment depicted in a drawing. The following detailed description is, therefore, not to be taken in a limiting sense, and the scope of the present invention is defined only by the appended claims.

The following definitions are provided to better define the present invention and to guide those of ordinary skill in the art in the practice of the present invention. Unless otherwise noted, terms are to be understood according to conventional usage by those of ordinary skill in the relevant art.

Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" can be used to describe the pressure applied to the tissue site, the actual pressure applied to the tissue site can be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

As used herein, the term "coupled" includes "indirect coupling" via a separate object. For example, a drape can be coupled to the tissue site if both the drape and the tissue site are coupled to one or more third objects, such as a release agent or a second adhesive layer. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond, and electrostatic coupling.

Various aspects of the present invention comprise a system and method for facilitating removal of a drape 125 from a tissue site 105, a portion of which is shown in each of the FIGS. 1-3. Various embodiments can facilitate the removal of the drape 125 from the tissue site 105 with less trauma to a patient than conventional drapes. The tissue site 105 may be skin tissue, wound tissue, bone tissue, or any other type of tissue. Various embodiments of the system and method described herein comprise, or can be used with, reduced pressure wound healing technology. For example, various embodiments described herein can be used in high-fluid transfer wound applications as can be found in, for example, some V.A.C. Instill® applications manufactured by Kinetic Concepts, Inc. (San Antonio, Tex.).

Figure 1B:
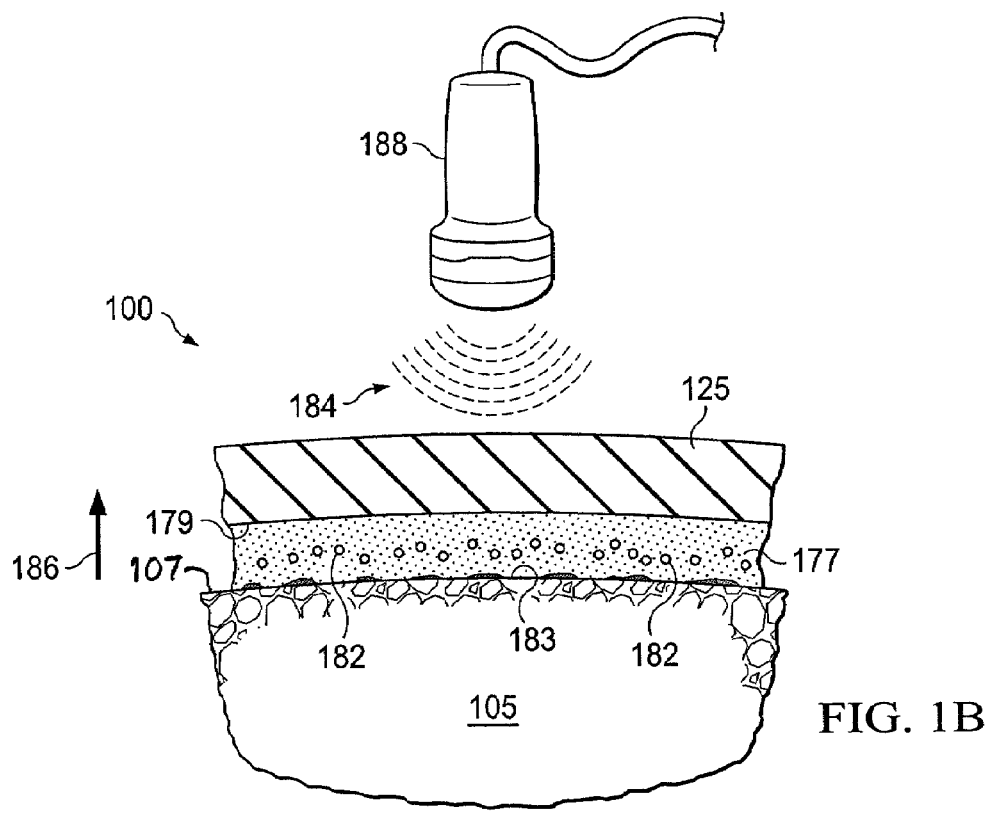
FIG. 1B is a cross-sectional view of a system for facilitating removal of a drape 125 from a tissue site 105 in accordance with an illustrative embodiment of the present invention.

Referring more specifically to FIGS. 1A and 1B, an illustrative embodiment of a drape removal facilitation system is shown generally at 100. The system 100 comprises the drape 125 having an adhesive side 179 and an adhesive layer 177 coupled to the adhesive side 179 of the drape 125. The adhesive layer 177 adheres to the tissue site 105 thereby coupling the drape 125 to the tissue site 105. The adhesive layer 177 may cover any portion of the drape 125 and the tissue site 105 as may be required. The adhesive layer 177 includes release agents comprising a release material 182, which may be contained in microstructures. The weakened bond that occurs as a result of the release of release material 182 allows a user of the drape removal facilitation system 100 to apply an upward force on drape 125, such as a force indicated by arrow 186, to remove drape 125 from tissue site 105. The weakened bond reduces the stress applied to tissue site 105 in the removal of drape 125 from tissue site 105. Thus, a patient feels less pain and discomfort when the drape 125 is removed. A residue of molecules from adhesive layer 177 might remain on tissue site 105 after removal of drape 125 depending on a variety of factors such as the type of release agent used.

Referring more specifically to FIG. 1A, release materials 182 are inertly dispersed within adhesive layer 177 and are located at the interface between adhesive layer 177 and tissue site 105. But release materials 182 can be located anywhere within adhesive layer 177, as well as any of the outer surfaces of adhesive layer 177, such as the interface between adhesive layer 177 and drape 125. In some embodiments, release materials 182 can be bonded or coupled directly to drape 125, and a separate film layer, not shown in FIG. 1A, can separate release materials 182 from adhesive layer 177. In these embodiments, the presence of an external stimulus 184 (not shown) can weaken, break-down, or increase the permeability of the separate film layer such that release materials 182 are allowed to migrate into adhesive layer 177 to facilitate the removal of drape 125 from tissue site 105. Release materials 182 in FIG. 1A are released in the presence of external stimulus 184 such that release materials 182 are allowed to migrate within adhesive layer 177 and the interface between adhesive layer 177 and tissue site 105.

Referring more specifically to FIG. 1B, drape removal facilitation system 100 is shown according to an illustrative embodiment. In particular, drape removal facilitation system 100 shows a non-limiting example of drape removal facilitation system 100 that is exposed to an external stimulus 184. Source 188 can emit external stimulus 184. A presence of an external stimulus 184 can cause microstructures containing release agents comprising a release material 182 to rupture or tear, thereby releasing release materials 182 from the interior of the microstructures. These released release materials 182 can then be interspersed into adhesive layer 177 and the interface between adhesive layer 177 and tissue site 105, thereby weakening the bond between drape 125 and tissue site 105 and facilitating the removal of drape 125 from tissue site 105.

The migration of release materials 182 can form pores 183 at the surface of the adhesive layer 177 adjacent the tissue site 105 which facilitate the removal of drape 125 from tissue site 105. Although FIG. 1B shows pores 183 to be at or near the interface between adhesive layer 177 and tissue site 105, pores 183 can be located anywhere in adhesive layer 177, including any surface of adhesive layer 177. For example, pores 183 can be located at the interface between drape 125 and adhesive layer 177.

Where release materials 182 comprise or form gas particles, the presence of external stimulus 184 causes the gas particles in adhesive layer 177 to be released from their inert state to form pores 183, which can be filled with the gas particles. In one example, pores 183 are formed as a result of either or both of the expansion or migration of the gas particles. As described above, the presence of external stimulus 184 can also cause a reaction between at least two substances in adhesive layer 177 that generate the gas particles to form pores 183. The release or generation of the gas particles causes an increase in the porosity in adhesive layer 177 that facilitates the removal of drape 125 from tissue site 105. For example, pores 183 can weaken the bond between the molecules within adhesive layer 177. This weakening can be a result of the spatial separation of the molecules in adhesive layer 177 and tissue site 105 or can also be a result of the poor bonding qualities between the molecules in the gas particles and the molecules in adhesive layer 177 and tissue site 105.

Where release materials 182 comprise oil particles, the presence of external stimulus 184 causes the oil particles in adhesive layer 177 to be released to form pores 183, which can be filled with the oil particles. The presence of oil-filled pores 183 weakens the bond between adhesive layer 177 and tissue site 105. For example, pores 183 can prevent the molecules in adhesive layer 177 from bonding to tissue site 105 by spatially separating the molecules in adhesive layer 177 and tissue site 105. Also, the chemical composition of the oil particles in pores 183 can be such that the molecules in adhesive layer 177 and tissue site 105 form little or no bond with the molecules in the oil particles.

Where release materials 182 are contained by microstructures, the presence of external stimulus 184 can cause the microstructures to rupture such that release materials 182 are released in adhesive layer 177 to form pores 183 containing the release agent. For example, the microstructure can be composed of material that is weakened, destabilized, or cleaved by external stimulus 184, thereby allowing release materials 182 contained in the microstructures to be released.

Where release materials 182 are contained by micelle microstructures, the molecules forming the micelle, such as the surfactant molecules, can be dissociated in the presence of external stimulus 184, thereby causing a rupture that allows release materials 182 to be released. In one embodiment, the molecules in the micelle are dissociated in the presence of external stimulus 184 that is ultrasound pulses in a range of 20 to 90 kilohertz. Release materials 182 can also be released from the micelles by altering the permeability of the micelles. For example, external stimulus 184 can be light that affects the permeability of the micelles such that release materials 182 can exit the micelles. In this example, photo-oxidation of the micelle allows release materials 182 to be released.

Figure 2A:
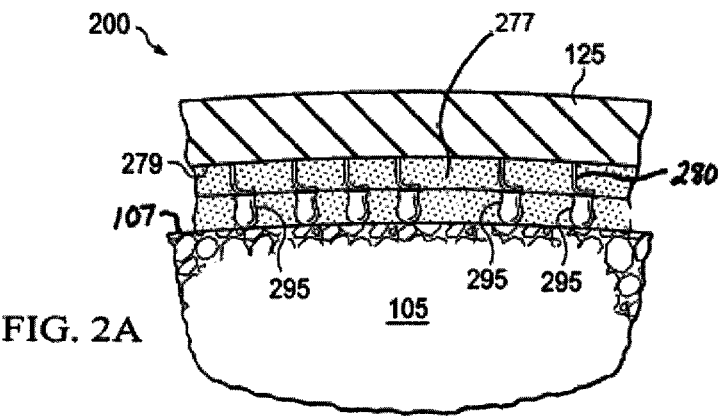
FIG. 2A is a cross-sectional view of a system for facilitating removal of a drape 125 from a tissue site 105 in accordance with an illustrative embodiment of the present invention.

Turning now to FIG. 2A, an illustrative embodiment of a drape removal facilitation system is shown generally at 200. In FIG. 2A, no external stimulus is being applied to drape removal facilitation system 200. Drape removal facilitation system 200 includes adhesive layer 277 on adhesive side 279 of drape 125. In FIG. 2A, drape removal facilitation system 200 includes a release agent comprising a layer of linker material 295. The layer of linker material 295 is coupled to adhesive layer 277 via functional group 280. Drape 125 is adapted to be coupled to tissue site 105 via layer of linker material 295. In particular, layer of linker material 295 can be adapted to bond directly to tissue site 105.

Figure 2B:
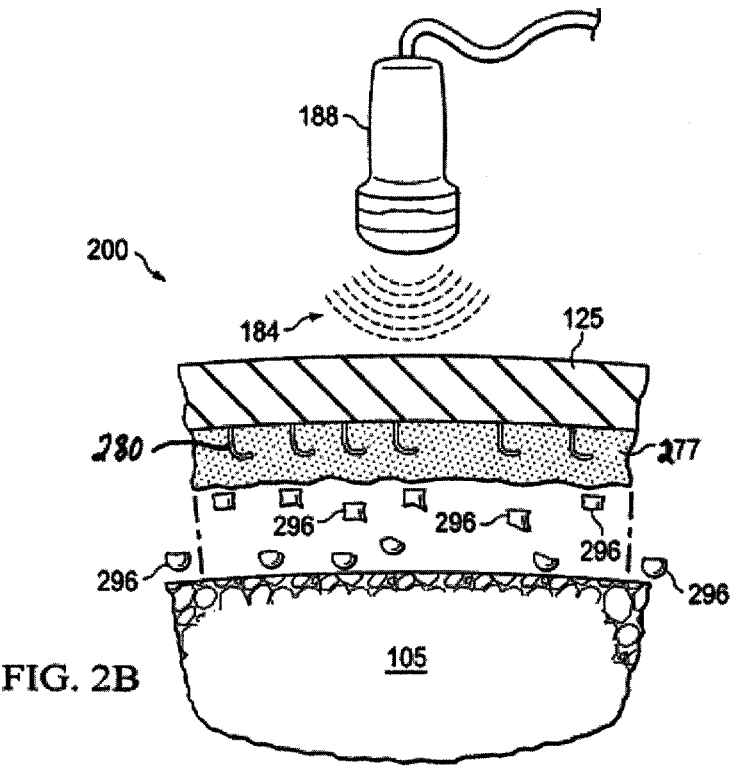
FIG. 2B is a cross-sectional view of a system for facilitating removal of a drape 125 from a tissue site 105 in accordance with an illustrative embodiment of the present invention.

Turning now to FIG. 2B, drape removal facilitation system 200 is shown according to an illustrative embodiment. In particular, FIG. 2B shows a non-limiting example of drape removal facilitation system 200 that is exposed to an external stimulus 184. External stimulus 184 cleaves linker material 295 into cleaved linker material 296. Thus, the bond between adhesive layer 277 and tissue site 105 is weakened or broken to facilitate the removal of drape 125 from tissue site 105. In the depicted embodiment, the adhesive layer 277 retain functional groups 280 after cleavage of linker material 295. Drape 125 can then be removed from tissue site 105 without undue stress being placed on tissue site 105. In FIG. 2B, where the layer of linker material 295 comprises photolabile linkers, external stimulus 184 can be light that cleaves the photolabile linkers into cleaved linker material 296. Because no adhesive layer is present between the layer of linker material 295 and tissue site 105, little or no adhesive layer residue remains at tissue site 105 upon the removal of drape 125 from tissue site 105.

Figure 3A:
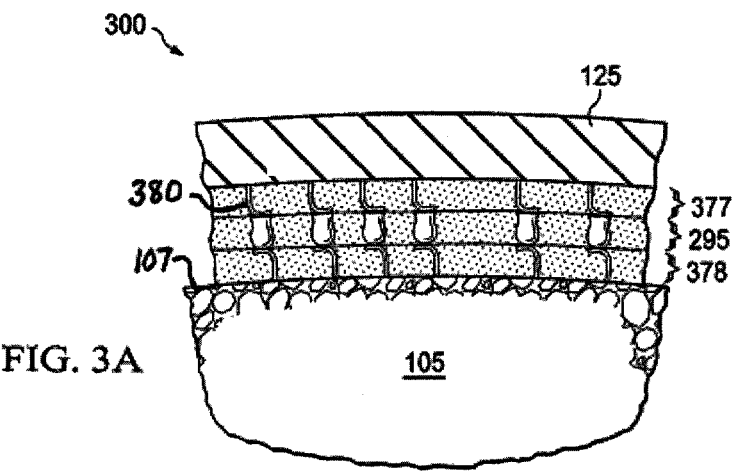
FIG. 3A is a cross-sectional view of a system for facilitating removal of a drape 125 from a tissue site 105 in accordance with an illustrative embodiment of the present invention.

Turning now to FIG. 3A, drape removal facilitation system 300 is shown according to an illustrative embodiment. In FIG. 3A, no external stimulus is being applied to drape removal facilitation system 300. In the non-limiting example shown in FIG. 3A, the portion of tissue site 105 shown can be skin tissue. However, the portion of tissue site 105 shown in FIG. 3A can also include any other type of tissue, such as wound tissue or bone, as discussed further below.

In FIG. 3A, the drape removal facilitation system 300 includes a first adhesive layer 377 and a second adhesive layer 378. Second adhesive layer 378 is adapted to bind to tissue site 105. Drape removal facilitation system 300 includes a release agent comprising a layer of linker material 295. In the embodiment of FIG. 3A, the layer of linker material 295 does not bind directly to tissue site 105, but rather, binds to functional group 280 in second adhesive layer 378. Thus, one side of layer of linker material 295 is bound to first adhesive layer 377 and another side of the layer of linker material 295 is bound to second adhesive layer 378. In this manner, the layer of linker material 295 is sandwiched between first adhesive layer 377 and second adhesive layer 378.

Figure 3B:
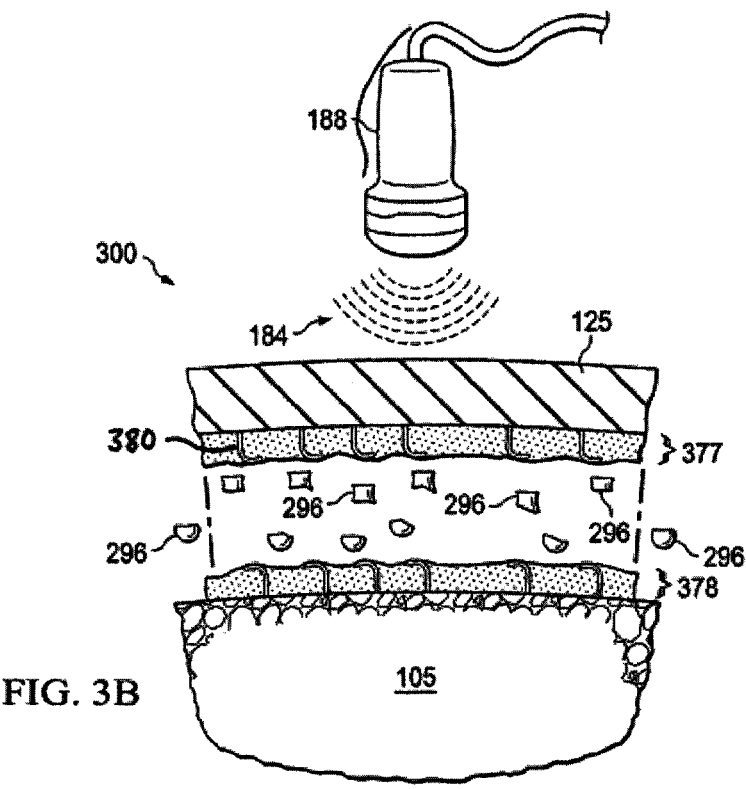
FIG. 3B is a cross-sectional view of a system for facilitating removal of a drape 125 from a tissue site 105 in accordance with an illustrative embodiment of the present invention.

Turning now to FIG. 3B, drape removal facilitation system 300 is shown according to an illustrative embodiment. In FIG. 3B, drape removal facilitation system 300 is exposed to an external stimulus 184. External stimulus 184 cleaves linker material 295 into cleaved linker material 296. Thus, the bond between first adhesive layer 377 and second adhesive layer 378 via linker material 295 is weakened or broken to facilitate the removal of drape 125 from tissue site 105. In the depicted embodiment, the first adhesive layer 377 and second adhesive layer 378 retain functional groups 380 after cleavage of linker material 295. Drape 125 can then be removed from tissue site 105 without undue stress being placed on tissue site 105. In the embodiment of FIG. 3B, all or a portion of second adhesive layer 378 can remain at tissue site 105 upon the removal of drape 125 from tissue site 105.

Also, the illustrative embodiments described in FIG. 1 can be used in combination with the illustrative embodiments described in FIGS. 2-3. For example, release agents comprising a release material 182 or microstructures containing release material 182 can be included in the illustrative embodiment described in FIGS. 2-3. In this example, the presence of external stimulus 184 can cleave linker material 295 and release release material 182 into the area between drape 125 and tissue site 105. Thus, the cleaving of linker material 295 can facilitate the migration of release material 182 in the area between drape 125 and tissue site 105.

Figure 4:
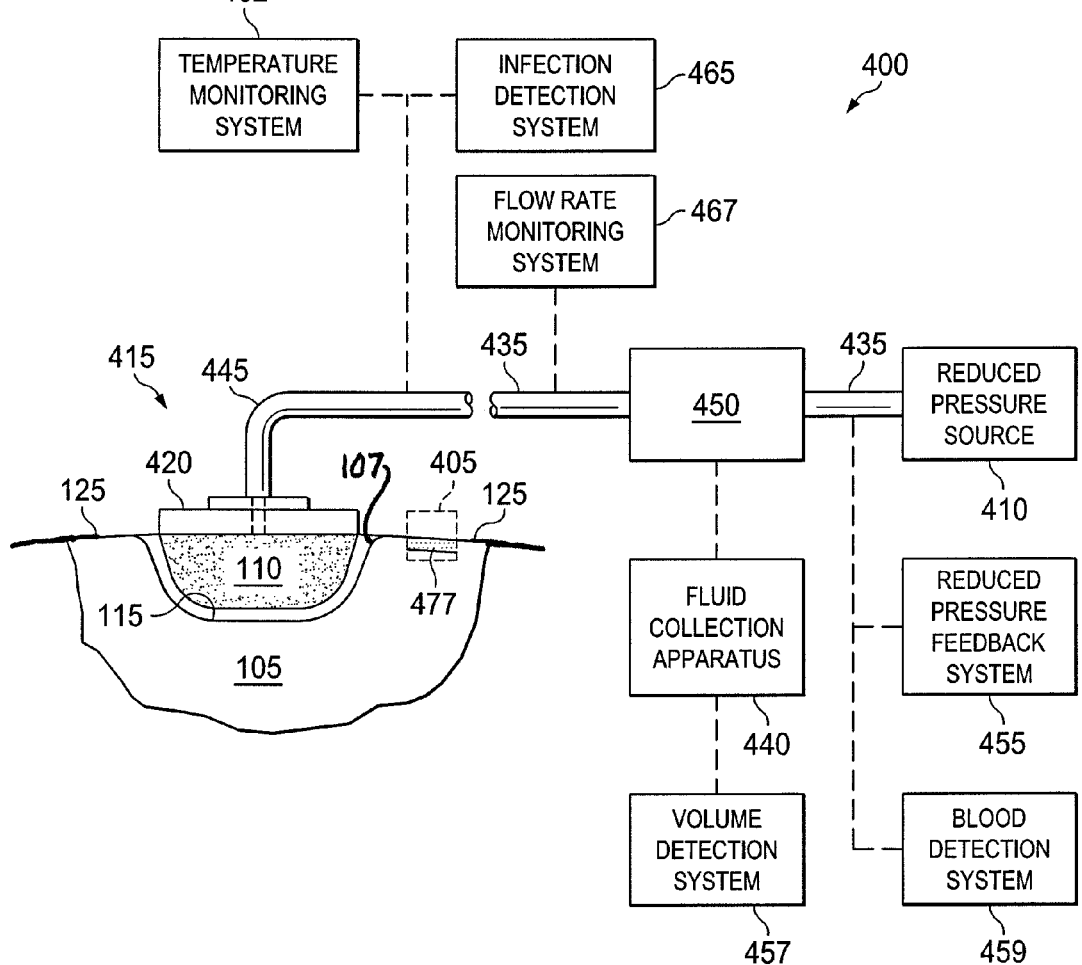
FIG. 4 is a block diagram of an apparatus for facilitating removal of a drape 125 from a tissue site 105 in accordance with an illustrative embodiment of the present invention.

Referring now to FIG. 4, a reduced pressure treatment system 400 is shown according to an illustrative embodiment. The reduced pressure treatment system 400 comprises a reduced pressure source 410 that provides a reduced pressure and dressing 415 connected to the reduced pressure source 410 via conduits 435 for delivering the reduced pressure to the tissue site 105. The dressing 415 comprises the drape 125, a delivery conduit 445, a connector 420 for supporting the delivery conduit 445 on the drape 125, and a foam pad 110 for insertion into the wound portion 115 of the tissue site 105. The drape 125 seals the foam pad 110 within the wound portion 115 of the tissue site 105 allowing the delivery conduit 445 to communicate a reduced pressure to the foam pad 110. The application of reduced pressure to tissue site 105 can be used to promote the drainage of exudate and other liquids from tissue site 105, as well as stimulate the growth of additional tissue. At any time before, during, or after the application of reduced pressure to tissue site 105, drape 125 can be removed for any reason as determined by the patient or administrator of reduced pressure treatment system 400 according to compositions and methods described herein.

Tissue site 105 can be the bodily tissue of any human, animal, or other organism, including bone tissue, adipose tissue, muscle tissue, dermal tissue, vascular tissue, connective tissue, cartilage, tendons, ligaments, or any other tissue. While tissue site 105 can include a wound, diseased tissue, or defective tissue, the tissue site 105 can also be healthy tissue that is not wounded, diseased, or defective. The tissue site 105 has a tissue surface 107 surrounding the wound portion 115 of the tissue site 105 to which the adhesive portion of the drape 125, for example, adhesive layers 177, 277, 377 and 378, adheres. The non-adhesive portion of the drape 125 covers the wound portion 115 of the tissue site 105. In other embodiments, however, the adhesive portion of the drape may cover some or all of the wound portion 115 of the tissue site 105 or the foam pad 110. When this occurs, the drape removal systems 100, 200, 300 facilitate removal of the drape 125 because they require substantially less force as compared to a conventional drape. Such systems can tolerate the adhesive portion of drape 125 partially covering the wound portion 115 of the tissue site 105 that would be otherwise difficult or impossible to securely dress with conventional drapes.

Drape 125 can be configured to provide a sealed connection with the tissue surface 107 of the tissue site 105 surrounding the wound portion 115. The sealed connection is provided by any one of the adhesive layers 177, 277, 377 and 378 positioned along a perimeter of the drape 125 or on any portion of drape 125 to secure drape 125 to the tissue surface 107 of the tissue site 105 surrounding the wound portion 115. The adhesive layers can be pre-positioned on drape 125 or can be sprayed or otherwise applied to drape 125 immediately prior to installing drape 125. Prior to the application of drape 125 to tissue site 105, the adhesive can also be covered by an adhesive support layer. The adhesive support layer can provide rigidity to the drape 125 prior to application and can also aid in the actual application of drape 125 onto tissue site 105. The adhesive support layer can be peeled off or otherwise removed before applying drape 125 to tissue site 105. A portion of any one of the drape removal facilitation systems 100, 200, 300 is shown and collectively referred to as drape removal systems 405.

Reduced pressure treatment system 400 also includes a fluid collection apparatus 440. Liquids from the wound portion 115 of the tissue site 105, such as exudates, flow through delivery conduit 445 and the conduit 435 into fluid collection apparatus 440 via a connector 450 that also communicates the reduced pressure from the reduced pressure source 410 to the delivery conduit 445. The reduced pressure treatment system 400 can further include a volume detection system 457 to detect the amount of fluid present in fluid collection apparatus 440; a reduced pressure feedback system 455; a blood detection system 459 to detect the presence of blood in exudate drawn from the wound portion 115 of the tissue site 105; a temperature monitoring system 462 to monitor the temperature of tissue site 105; an infection detection system 465 to detect the presence of infection at tissue site 105; or a flow rate monitoring system 467 to monitor the flow rate of fluids drawn from tissue site 105. In addition to the above-mentioned components and systems, reduced pressure treatment system 400 can include valves, regulators, switches, and other electrical, mechanical, and fluid components to facilitate administration of reduced pressure treatment to the wound portion 115 of the tissue site 105.

The following sections describe components of the drape removal system 405 in more detail including the following: the drape 125; the adhesive layers 177, 277, 377 and 378 referred to collectively as adhesive layer 477 as shown in FIG. 4; a release agent 482 (not shown) comprising one or more of the release materials 182, linker materials 295, or any other similar materials; the release materials 182; microstructures; the linker materials 295; and the external stimulus 184.

1. Drape 125

A drape 125 is generally understood to be a covering over a tissue site 105. A drape 125 can function to secure one or more components of the system to a tissue site 105. For example, a drape 125 can secure an optional manifold to a tissue site 105. A drape 125 is preferably sterilizable. A drape 125 can comprise a biocompatible thin film material, such as a polymer. A drape 125 can comprise a woven or non-woven material. A drape 125 can comprise an elastic or non-elastic material. A drape 125 can comprise a flexible or inflexible material. A drape 125 of inflexible material can be molded for a particular tissue site 105. Preferably, the drape 125 is a soft, flexible material having skin-like conformability. A drape 125 can comprise an impermeable, semi-permeable, or permeable material. Permeability characteristics can be selected according to desired moisture and gas (e.g., oxygen) transmission. In some embodiments, the drape 125 comprises a material relatively impermeable to moisture and relatively permeable to oxygen. A drape 125 can be coated with a material, for example, to control breathability. A drape 125 can comprise an occlusive or nonocclusive material. An occlusive dressing can be desirable to increase uptake of a therapeutic agent supplied to a tissue site 105.

A drape 125 can comprise a material which allows or facilitates transmission of external stimuli, such as light, sound, moisture or heat. For example, a drape 125 material can be semi- or substantially transparent to electromagnetic radiation, such as visible, ultraviolet, or infrared light. As another example, a drape 125 material can facilitate transmission of ultrasonic energy. Fiber containing materials are often opaque due to the light scattering effect of the fibers. The scattering can be reduced by impregnating the fiber-containing material with another material of similar refractive index (as the fibers) to provide semi- or substantially translucent or transparent material better able to transmit electromagnetic radiation, such as visible, ultraviolet, or infrared light. Relatively "simple" polymers, such as a polyolefin, having few active chemical species can absorb less electromagnetic radiation, such as visible, ultraviolet, or infrared light, than such polymers as polyurethane, polyester, & polyamide, which have significant levels of active chemical groups (e.g. amine, ester, carboxyl, hydroxyl, ether, aromatic, and double bond saturation).

Materials of a drape 125 can be selected so as to promote one or more of stemming bleeding, absorbing exudate, easing pain, debriding a wound, controlling moisture content, controlling rate of absorption of a topical medicament, maintaining pH, maintaining temperature, protecting from infection, indicating increased bioburden levels, and promoting healing. A drape 125 preferably comprises a biocompatible material that includes the impermeability or permeability characteristics desired or necessary for a tissue site 105. For example, a drape 125 can be formed of a hydrophobic material to prevent moisture absorption by the drape 125. A drape 125 can take the form of, for example, a film, gel, foam, paste, granule, or bead. As an example, a drape 125 can be in sheet form. As another example, a drape 125 can be in a flowable form suitable for pouring or dispensing by other means known in the art. As another example, a drape 125 can be in a sprayable form. A drape 125 can be applied after or simultaneously with other system components such as a manifold or an adhesive layer 177.

A drape 125 can be composed of materials including, but not limited to, polyurethane, polyether, polyester, polyolefin, polyolefin sintered polymer, silicone based compound, acrylic, alginate, hydrocolloid, hydrogel, hydrogel-forming material, polysaccharide, natural fabric, synthetic fabric, polyvinyllchlorides, polyamides, polyethyl eneglycolpolydimethyl diloxan co-polymers, polyphosphazenes, cellulosic polymers, chitosan, PVdF, EVA sintered polymer, PTFE, thermoplastic elastomers (TPE), or combinations thereof. Preferably, a drape 125 comprises a thin film biocompatible polymer. Combinations can be polymeric combinations, layered combinations, or both. For example, the drape 125 can comprise an EVA sintered polymer. As another example, the drape 125 can comprise Tyvek (PE), especially in the function of a protective cover. Commercially available exemplary drape 125 materials include, but are not limited to, Avery Dennison Med 5625; 3M Ioban2; 3M Steri-Drape 125 2; Nitto Denko Yu-Kiban Perme; 3M Tegaderm; First Water Hydroskin; Opsite; Exopack (a polyurethane film and adhesive); Bayer (a polyurethane film); DuPont (an etherester film).

A drape 125 can be composed of one or more layers. In some embodiments, a drape 125 can be a bilayer drape 125. For example, a bilayer drape 125 can comprise a first layer comprising any biocompatible thin film suitable for tissue or wound contact and a second layer comprising a protective material, such as moisture resistant Tyvek (PE). As another example, a drape 125 can comprise a (second layer) coating to control breathability. Three, four, or more drape 125 layers are contemplated, with combinations of materials selected according to desired function. In some embodiments, the drape can comprise zones of the same or different materials. For example, within the same plane, multiple zones can comprise differing drape 125 material. As another example, a drape 125 can include both a laminate structure comprising a plurality of drape 125 materials and multiple zones of materials within the same plane.

A drape 125 can be manufactured by laminating an adhesive-coated flexible film, such as a polyurethane film, to a protective releasable layer, such as a siliconized paper. A strengthening layer of thicker plastic material, e.g. a polyolefin such a polyethylene, can be applied to a non-adhesive coated face of the flexible film, so that a three-layer laminate is produced. A laminate can be produced in a substantial width and can be slit longitudinally to a desired width and then laterally to form a drape 125 of desired dimensions. Handling bars can be applied to an adhesive-coated layer at one or both lateral edges to facilitate separation of the film from the protective, releasable layer.

In some embodiments, a drape 125 is able to maintain a reduced pressure at a tissue site 105 after installation of the drape 125. At any time before, during, or after the application of reduced pressure to a tissue site 105, a drape 125 can be removed for any reason as determined by the patient or caregiver.

A drape 125 can include a device that provides sealing functionality. For example, a drape 125 can include a suction cup, a molded cast, or a bell jar. Such devices, or other devices providing sealing functionality, can be applied over other components of the system, such as the manifold, dressing, adhesive layer 177, or other portions of the drape 125.

A drape 125 can be configured to provide a sealed connection with tissue surrounding the system, or components thereof, and the tissue site 105. A sealed connection can be provided by an adhesive layer 177 positioned along a perimeter of a drape 125 or on any portion of drape 125 so as to secure the drape 125 to other components of the system (e.g., manifold), tissue surrounding the tissue site 105, or combinations thereof.

2. Adhesive Layer 477

The system can include an adhesive layer 477. The adhesive layer 477 can function to secure one or more components of the system, such as a drape 125, to a tissue site 105. The adhesive layer 477 is preferably located on the drape 125, such as an adhesive side of the drape 125. An adhesive layer 477 can be adapted to bind to a tissue site 105. An adhesive layer 477 can comprise any material, in single or multiple layers, capable of adhering to a surface, such as a tissue site 105. In some embodiments, a drape 125 is bound to a tissue site 105 via an adhesive layer 477. In one example, an adhesive layer 477 can be pre-applied to an adhesive side of a drape 125 prior to application to a tissue site 105.

An adhesive layer 477 can cover an entire surface of a drape 125 or only a portion of a of a drape 125. For example, an adhesive layer 477 can cover a portion of the adhesive side of a drape 125. Adhesive covered portions can form any suitable shape. For example, an adhesive layer 477 can form a circle, square, or strip across a drape 125 such that only those portions of a drape 125 covered by an adhesive layer 477 are adapted to adhere to a tissue site 105.

An adhesive can be pre-positioned on a drape 125 or can be sprayed or otherwise applied to the drape 125 prior to installation. Prior to the application of a drape 125 to a tissue site 105, the adhesive can also be covered by an adhesive support layer. The adhesive support layer can provide rigidity to the drape 125 prior to application and can also aid in the actual application of drape 125 onto tissue site 105. The adhesive support layer can be peeled off or otherwise removed before applying a drape 125 to a tissue site 105.

An adhesive layer 477 can comprise a material capable of adhering to a surface, such as a tissue site 105 or other component of the system. An adhesive layer 477 can comprise one or more materials including, but not limited to, polyurethane, acrylic (e.g., cyanoacrylate), hydrogel, silicon or silicone based material, natural rubber, synthetic rubber, styrene block copolymers, polyvinyl ethers, poly(meth)acrylates, polyolefins, hydrocolloid (e.g., a rubber based hydrocolloid), or a combination thereof. In some embodiments, the adhesive layer 477 comprises a polymer or co-polymer. For example, the adhesive layer 477 can comprise a co-polymer of polyurethane and silicone or various acrylic co-polymers.

An adhesive layer 477 can have any thickness suitable to facilitate securing the system, or components thereof, to a tissue site 105 or surrounding tissue. For example, an adhesive layer 477 can have a thickness of about 0.1 mm to about 50 mm. Thickness of an adhesive layer can depend upon adhesive contained therein. For example, an acrylic and rubber containing adhesive layer can have a thickness of about 0.5 mm to about 5 mm, preferably about 1 mm to about 2 mm. As another example, a silicone gel containing adhesive layer can have a thickness of about 4 mm to about 15 mm. As another example, a hydrogel containing adhesive layer can have a thickness of about 10 mm to about 40 mm. As another example, a hydrocolloid containing adhesive layer can have a thickness of about 4 mm to about 40 mm, preferably about 10 mm to about 40 mm. Thickness can further vary according to additional components of the adhesive layer. For example, a V.A.C. hydrogel with PEG can have a thickness of about 3 mm to about 4 mm. A relatively thicker adhesive layer 477 can allow for the presence of more microstructures or release agents 182 or larger microstructures. An adhesive layer 477 can have a uniform thickness or a non-uniform thickness.

A residue of molecules from an adhesive layer 477 can or can not remain on a tissue site 105 after removal of a drape 125 depending on a variety of factors, including, but not limited to, the location of pores, the type of release agent used, or the particular embodiment implemented. In some embodiments, no residue of molecules from an adhesive layer 477 remain on a tissue site 105 after removal of a drape 125.

The side of an adhesive layer 477 adapted to bind to a tissue site 105 can be covered by an adhesive support layer. The adhesive support layer can be removed prior to the application of a drape 125 to a tissue site 105. The adhesive support layer can provide rigidity to a drape 125 prior to application. The adhesive support layer can facilitate in the actual application of a drape 125 onto a tissue site 105. In one example, an adhesive support layer covers only a portion or portions of a drape 125 covered, in whole or in part, by an adhesive layer 477. In another example, an adhesive support layer can cover portions of a drape 125 covered by an adhesive layer 477 and portions not covered by an adhesive layer 477. An adhesive support layer can comprise a single segment or a plurality of segments, each covering a different portion of a drape 125 or adhesive layer 477.

An adhesive support layer can serve to protect a drape 125, an adhesive layer 477, a release material 182, or a linker material 295, or a combination thereof, from an external stimuli. An adhesive support layer can protect a drape removal system from an external stimulus 184 that can cause release or activation of a release material 182 or cleavage of a linker material 295. For example, in a drape removal system comprising a photolabile linker, an adhesive support layer can be chosen so as to block transmission of light.

In one embodiment, the system includes an adhesive tape. The adhesive tape can include a backing layer and an adhesive layer 477. An adhesive tape can be used to hold primary or secondary dressings in place. An adhesive tape can serve a function as both a tissue site cover and adhesive layer 477 thereof. A backing layer of an adhesive tape can comprise a material such as those discussed above in the context of a drape 125. Preferably, the backing layer of the adhesive tape comprises cloth, polyurethane, or non-woven materials.

Fiber containing materials are often opaque due to the light scattering effect of the fibers. The scattering can be reduced by impregnating the fiber-containing material with another material of similar refractive index (as the fibers) to provide semi- or substantially translucent or transparent material better able to transmit electromagnetic radiation, such as visible, ultraviolet, or infrared light.

Relatively "simple" polymers, such as a polyolefin, having few active chemical species can absorb less electromagnetic radiation, such as visible, ultraviolet, or infrared light, than such polymers as polyurethane, polyester, & polyamide, which have significant levels of active chemical groups (e.g. amine, ester, carboxyl, hydroxyl, ether, aromatic, and double bond unsaturation).

3. Release Agents 482

A release agent 482 comprising a release material 182 can facilitate removal of a drape 125 from a tissue site 105. The release agent 482 can physically or chemically affect adhesion characteristics between a drape 125 and a tissue site 105. Release agents can be present in an inert or inactive form in, on, or near an adhesive layer 477. For example, a release agent 482 can be mixed with the adhesive; on the surface of the adhesive with a random or patterned coverage; coupled to the drape 125 with a random or patterned coverage; or contained within a microstructure located in these or other locations. Upon release or activation, release agents 482 can migrate within the adhesive layer 477 or along an interface between an adhesive layer 477 a tissue site 105 to facilitate the removal of a drape 125 affixed thereto. Techniques such as differential scanning calorimetry (DSC), rheometry, a mechanical tensile test device can be used to optimize levels of release agents in or on the adhesive layer 477.

4. Release Materials

In some embodiments, the release agent comprises a release material 182. Release material 182 can be inertly dispersed within an adhesive layer 477. Release material 182 can be located at the interface between an adhesive layer 477 and a tissue site 105. It is contemplated that a release material 182 can be located anywhere within an adhesive layer 477, as well as any outer surface of an adhesive layer 477, such as an interface between the adhesive layer 477 and drape 125. In some embodiments, a release material 182 can comprise a microstructure. For example, a release material 182 can form a microstructure. As another example, a release material 182 can be encapsulated in a microstructure. Suitable microstructures can be as discussed below. In some embodiments, a release material 182 can be a component of an adhesive of the adhesive layer. Where a release agent functions to chemically interfere with, weaken, or otherwise disrupt a bond, it is usually comprises a linker material 295.

A release material 182 can released in the presence of an external stimulus 184, as discussed further below. In some embodiments, release material 182 is bound to an adhesive layer 477 in an absence of any external stimulus 184 that is capable of weakening or breaking the bond between the release material 182 and adhesive layer 477. For example, a release material 182 can be bound to an adhesive layer 477 via a chemical bond or by virtue of physically abutting the adhesive layer 477. In some embodiments, a release material 182 is mixed into an adhesive layer 477.

In some embodiments, a release material 182 can be bonded to the drape 125. In some embodiments, a release material 182 can be coupled to a drape 125. For example, a separate film layer of the drape 125 can release a release material 182 from an adhesive layer 477. The presence of an external stimulus 184 can weaken, break-down, or increase the permeability of a separate film layer such that release agents 482 are allowed to migrate into the adhesive layer 477 to facilitate the removal of the drape 125 from a tissue site 105.

In some embodiments, the system includes a plurality of release materials 182 bound to the adhesive layer 477 that are released in the presence of the external stimulus 184 to facilitate removal of the drape 125 from the tissue site 105. In another embodiment, the system includes a first adhesive layer 477 on the adhesive side of the drape 125. The system can also include a plurality of linker materials 295 coupled to the first adhesive layer 477. The drape 125 can be adapted to be coupled to the tissue site 105 via a plurality of linker materials 295. The plurality of linker materials 295 can be weakened in the presence of the external stimulus 184 to facilitate removal of the drape 125 from the tissue site 105.

A release material 182 can function, for example, according to chemical or physical interaction with an adhesive or other component of the system. In some embodiments, a release material 182 can react with an adhesive, with itself, or with some other component of the system so as to change the character of the drape 125 adhesion to the tissue site 105. For example, a release material 182 can react, resulting in hardening (e.g., through crosslinking), softening (e.g., oxidation degradation, chain scission), or dissolving (e.g., release of solvent) of the adhesive layer, the drape, or the release agent itself.

In some embodiments, a release material 182 can physically interact with an adhesive. A release material 182 can, for example, stimulate a cohesive fracture, interfacial fracture, mixed fracture, or alternating crack path fracture in the adhesive layer. Release of a release material 182 can form pores that facilitate the removal of a drape 125 from a tissue site 105. For example, a release material 182 can react so as to form bubbles, thereby pushing the adhesive away from a tissue site 105.

A release material 182 can comprise a variety of molecular compositions depending on the particular embodiment being implemented. A release material 182 can comprise a sub-ambient $T_g$ material. Where a release material 182 comprises a sub-ambient $T_g$ material, cooling the system can trigger drape release. A sub-ambient $T_g$ material can be incorporated into or onto the adhesive layer. Upon cooling, a sub-ambient $T_g$ material can crystallize, thereby introducing brittleness to disrupt an adhesive layer, thereby facilitating removal of the drape 125. Examples of a sub-ambient $T_g$ material include, but are not limited to, Evonik Degussa DYNAPOL® LH 538 Polyester Resin; Evonik LTW adhesion resin; Loctite Durabond E-OOCL epoxy adhesive; and Loctite Durabond E-OONS epoxy adhesive.

A release material 182 can comprise a photopolymer. A photopolymerized release agent can be incorporated into or onto the adhesive layer 477. Photoinitiation of polymerization can result in a hard brittle material that can interfere with the adhesive layer 477, thereby facilitating removal of the drape 125. One example of a photopolymerizable release agent is bisphenol glycidylmethacrylate. Additional release agent components can include, but are not limited to, diluents, crosslinkers, coupling agents, free radical initiators, chemical accelerators, and plasticizers.

A release material 182 can comprise an oil particle. Examples of release materials 182 include, but are not limited to, natural oils, synthetic oils, surfactants, silicone particles, paraffin particles, fluorocarbon particles, vitamin E, glycerin, glycerol, olive oil, safflower oil, sesame oil, tea tree oil, stearic acid, glycery stearate, retinyl palmitate, allantoin, soy esters or other appropriate esters, d-limonene or other appropriate terpenes, or a particle having a low melting point, or combinations thereof. As described in greater detail herein, the release of such particles in the presence of an external stimulus 184 can cause the bond between a drape 125 and a tissue site 105 to weaken, thereby facilitating the removal of the drape 125.

A release material 182 can comprise a solvent. A solvent can dissolve an adhesive so as to ease removal. Solvent release agents can be selected to minimize concerns of toxicity and adhesive residue. Examples of a solvent release agent include, but are not limited to, DMSO; IPA; ethyl acetate; and polyethylene glycol. One example of a solvent release agent is tetrahydrofurfuryl acetate to facilitate removal of a cyanoacrylate dermal adhesive.

A release material 182 can comprise a lipid. When released (e.g., melted), a lipid release agent can interfere with a bond between a tissue site and an adhesive. A lipid can be encapsulated within a microstructure or itself form a microstructure (e.g., a solid lipid nanoparticle). An example of a lipid release agent is solid lipid particles (Trilaurin with 0.01% Brij 78, with m.p. 45-47° C., average particle size 6.5 µm). Particle size of a solid lipid can be modulated through, for example, different emulsification techniques.

Other examples of release materials 182 include, but are not limited to: thermally degrading adhesives (e.g., high degree of Diels-alder adducts, heat to react); Gecko mimics (e.g., polyvinylsiloxane microscale pillars, carbon nanotubes, coated PDMS micropatterns, rippled PDMS films); ultrasonic degraded compounds (e.g., alkoxylate acrylate, pharma fillers, ultrasonics of about 20 kHz); thermally reversible adhesives; mussel adhesive proteins (e.g., mimics of mussel adhesion); polymer brushes (e.g., tethered polymer chains); solvent induced switching (e.g., polymer brushes, PS, PVP); magnetic on/off (e.g., MEMS device with cantilevered nanostructures moveable with a magnetic field); and silicone gel.

Further examples of release material 182 include any of the materials discussed below in the context of linker materials, where an external stimulus causes the polymer to react in such a way as to cause a physical disruption of the adhesive layer (i.e., the polymer material polymerizes so as to form a physical structure that interferes with the adhesive, rather than depolymerizing so as to disrupt adhesive bonds).

A release material 182 can comprise a gas particle. Examples of release materials 182 include, but are not limited to, nitrogen, helium, hydrogen, carbon dioxide, oxygen, and fluorocarbons, such as chlorofluorocarbons. For example, a volatile liquid (e.g., hydrocarbon) or gas can be encapsulated in a microstructure; when exposed to an external stimulus 184, such as a solvent or heat, the gas can be liberated. In some embodiments, the gas particles can be generated by a reaction between at least two substances, such as another release material 182, a linker material 295, or an adhesive material. For example, gas particles can be formed by a reaction between a linker material 295 and a material of the adhesive layer 477. Such a reaction can occur in the presence of an external stimulus 184, such as those described herein. As an example, an oxygen release agent can be produced from urea hydroperoxide via low pH or a solvent (e.g., an alcohol). As another example, a carbon dioxide release agent can be produced upon exposure of a mixture of tartaric acid and bicarbonate to water. As another example, calcium carbonate and citric acid can be separately encapsulated within a hydrogel microstructure and upon being release can form bubbles. In some embodiments, the release or generation of gas particles can cause an increase in the porosity of an adhesive layer 477, thereby weakening a bond between a drape 125 and a tissue site 105. Such weakening of an adhesive layer 477 can facilitate the removal of a drape 125 from a tissue site 105.

5. Microstructures

A microstructure can serve as a delivery vehicle for a release agent. In one embodiment, the system includes a plurality of microstructures bound to the adhesive layer 477. A release material 182 can be encapsulated in material of the microstructure, which can be embedded in or on the drape 125 where the microstructure remains dormant during drape 125 storage and application. A microstructure can contain one or more release materials 182 that are released in a presence of an external stimulus 184. Such release triggered by an external stimulus 184 can facilitate removal of a drape 125 from a tissue site 105. For example, a microstructure can comprise a material that is weakened, destabilized, or cleaved by an external stimulus 184, thereby allowing a release material 182 contained in the microstructures to be released.

A microstructures can be any shape, such as a sphere, prism, polygonal prism, cylindrical, or a bi-layer sheet in any of a variety of configurations. Microstructures can be uniformly or non-uniformly arranged. In one example, microstructures are located only in one or more designated zones of an adhesive layer 477. Such designated zones can form a shape, such as a circle, square, or stripe, in the adhesive layer 477. In some embodiments, microstructures are arranged equidistant from one another to form a grid-like matrix. In other embodiments, microstructures are configured to form an irregular pattern in which microstructures are not equidistant from one another. In further embodiments, microstructures are organized into a grid-like matrix in some regions and an irregular pattern in other regions.

A microstructure can comprise one or more carriers including, but not limited to, a polymeric delivery system, a microsphere, a polymeric hydrogel, a "smart" polymeric carrier, and a liposome. A microstructure can be composed of one or more materials including, but not limited to, natural polymers, such as collagen, polysachharides, and N-acetylglcosamines; synthetic polymers, such as silicone, latex, poly-lactide-co-glycolide, polyethylene vinyl-co-acetate, and polyanhydrides; polyvinyl alcohol; polyphosphazene; PLA; PLGA; PLGA coated with DPPC, DPPC, DSPC, or EVAc; gelatin; albumin; chitosan; dextran; cyclodextran; DL-PLG SDLMs; PEG (e.g., ProMaxx); sodium hyaluronate; a diketopiperazine derivative (e.g., Technosphere); a calcium phosphate-PEG particle; an oligosaccharide derivative (e.g., a DPPG such as Solidose); a hydrophillic polymer, such as collagen, fibrin, or alginate; polyalkylacrylic acid polymers; a lecithin, such as phosphatidylcholine, phosphatidylethanolamine, sphingomyelin, phosphatidylserine, phosphatidylglycerol, or phosphatidylinositol; a ceramic; glass. In some embodiments, a microstructure comprises at least two substances, such as acrylic polymer and a photoinitiator, such that in the presence of light, the acrylic polymer crosslinks, including shrinkage, stress, and fracture. In one example, a microstructure comprises a cyclodextrin, where the cyclodextrins can absorb and bind a release material 182, such as an oil particle, and then release the release material 182 upon being exposed to heat.

For example, a microstructure can comprise a polymeric delivery system comprising a natural polymer, such as collagen, or a synthetic polymer, such as silicone, poly-lactide-co-glycolide, polyethylene vinyl-co-acetate, or a polyanhydride. As another example, a microstructure can comprise a microsphere comprising PLA, PLGA, PLGA coated with DPPC, DPPC, DSPC, EVAc, gelatin, albumin, chitosan, dextran, DL-PLG, SDLMs, PEG, sodium hyaluronate, a diketopiperazine derivative, a calcium phosphate-PEG particle, or an oligosaccharide derivative. As another example, a microstructure can comprise a polymeric hydrogel comprising a hydrophillic polymer such as collagen, fibrin, and alginate. A smart polymer is generally understood to be a polymeric material that can change properties through the application of an external trigger. As an example, a microstructure can comprise so called "smart" polymeric carriers having pH-sensing functionality, such as a polyalkylacrylic acid polymer where pH profile can be controlled by the choice of the alkylacrylic acid monomer and by ratio of the carboxylate-containing alkylacrylic acid monomer to alkylacrylate monomer. Another example of a smart polymers for use as a microstructure material includes sub-ambient $T_g$ materials (e.g., Loctite; Evonik), which can provide brittleness to an adhesive once cooled below room temperature. Another example of a smart polymers for use as a microstructure material includes photocrosslinked dental composites, which can provide brittleness to an adhesive once exposed to UV light.

As another example, a microstructure can comprise a liposome (e.g., a reactive/polymorphic pH sensitive liposome) comprising one or more lecithins, such as phosphatidylcholines, phosphatidylethanolamines, sphingomyelins, phosphatidylserines, phosphatidylglycerols, and phosphatidylinositols.

In some embodiments, the microstructure itself comprises a release agent. For example, a release material 182 of vitamin E can be provided in the form of liposomes (e.g., Florasomes, a vitamin E liposome from Floratech).

In some embodiments, a microstructure is configured to be disrupted with the presence of an external stimulus 184, such as those described herein. For example, a microstructure can be configured to rupture or tear upon exposure to an external stimulus 184, thereby releasing a release material 182 from the interior of the microstructure. These released release materials 182 can be dispersed or interspersed into or onto an adhesive layer 477 or the interface between an adhesive layer 477 and a tissue site 105, thereby weakening a bond between a drape 125 and the tissue site 105 and facilitating the removal of the drape 125 from the tissue site 105.

A microstructure can be bonded to an adhesive layer 477 by one or more linker materials 295, as described more fully below. A microstructure can be physically embedded in an adhesive layer 477 without requiring the presence of a linker material 295. It is also contemplated that an adhesive layer 477 can comprise embedded microstructures not bound to a linker material 295 as well as microstructures bonded to the adhesive layer 477 by one or more linker materials 295.

In some embodiments, a microstructure comprises a micelle. A micelle is understood to be is an aggregate of surfactant molecules usually dispersed in a liquid colloid that can form a shape, such as a sphere. A micelle can be approximately spherical, ellipsoid, cylindrical, or bilayered. A wall of a micelle is generally composed of adjacent micelle molecules, such as surfactant molecules. When surfactants are present above a critical micelle concentration, the surfactants can act as an emulsifier that will allow a compound, such as a release agent, normally insoluble (in the solvent being used) to dissolve. Where a release agent is hydrophobic (or a non-polar solvent), a micelle can form an aggregate with hydrophilic "head" regions in contact with surrounding solvent, sequestering the hydrophobic tail regions in the micelle centre, otherwise known as normal phase micelle or oil-in-water micelle. Where a release material 182 is hydrophillic, an inverse micelles (i.e., a water-in-oil micelle) can have the headgroups at the centre with the tails extending out.

Examples of the compounds or compositions from which a wall of a micelle can be composed include, but are not limited to, polyethylene glycol (PEG), pluronics, phospholipids, lecithin, casein, a non-ionic surfactant, such as Brij 35, and mixed micelles consisting of ionic surfactants such as sodium dodecyl sulfate and non-ionic surfactants such as dodecyl maltoside.

Where microstructures are micelles, molecules forming the micelle, such as surfactant molecules, can be dissociated in the presence of an external stimulus 184, thereby causing a rupture that allows a release material 182 to be released. In one embodiment, molecules of a micelle are dissociated in the presence of an external stimulus 184 comprising ultrasound pulses in a range of 20 to 90 kilohertz. A release material 182 can be released from the micelles by altering the permeability of the micelles. For example, an external stimulus 184 such as light can effect a change (e.g., photooxidation) in the permeability of a micelle such that a release material 182 can exit the micelle.

A microstructure can be a coated microstructure. A coating of a microstructure can provide structural reinforcement, improve integration with another component of the system, enhance stability, or other desirable functions. Similarly, a microstructure can be modified so as to provide a structural feature that facilitates integration with another component of the system, such as bonding with an adhesive of the adhesive layer 477.

6. Linker Material 295

In some embodiments, the release agent 482 comprises a linker material 295. A linker material 295 is one or more molecules capable of bonding to another component of the system, such as a release material 182 or adhesive, or coupling other components. Bonding of a linker material 295 can be covalent bonding or ionic bonding. Disruption of a linker material 295 can facilitate removal of a drape from a tissue site, usually by disruption adhesive bonds.

In some embodiments, a release material 182 is bonded to an adhesive layer 477 by linker material 295. In some embodiments, a linker material 295 couples a release material 182 or microstructure and an adhesive layer 477. A linker material 295 and a release material 182 can be contained in the adhesive layer 477.

A linker material 295 can be bound to a second adhesive layer 477. For example, a linker material 295 can couple a first adhesive layer 477 and a second adhesive layer. In this manner, a linker material 295 can be sandwiched between adhesive layers, allowing such layers to easily separate upon disruption of the linker material 295.

Molecules of which an adhesive layer 477 is composed can have functional groups that chemically bond to a linker material 295. A drape 125 can be adapted to be coupled to a tissue site 105 via a linker material 295. A linker material 295 can be adapted to bond directly to a tissue site 105. For example, a linker material 295 can bond to a tissue site 105 via an electrostatic force or by virtue of a pH difference between any of an adhesive layer 477, linkers 295, and a tissue site 105. Examples of linker materials 295 capable of bonding directly to a tissue site 105 include, but are not limited to benzoin derivatives and hydrogels. In embodiments where no adhesive layer 477 is present between a linker material 295 and a tissue site 105, little or no adhesive layer residue remains at a tissue site 105 upon removal of a drape 125.

Bonding between a linker material 295 in the adhesive layer 477 and a release material 182 can render the release material 182 inert or immobile such that release material 182 do not weaken the adhesion between adhesive layer 477 and tissue site 105. Thus, a release material 182 can be prevented from acting prematurely.

The bond between a linker material 295 and a release material 182 or adhesive can be weakened or broken by exposure to an external stimulus 184, thereby facilitating removal of the system. A linker material 295 can become weak, unstable, or cleaved in the presence of external stimuli, such as light, sound, pressure, heat, and fluids, described further below. Preferably, a linker material 295 of the drape removal facilitation system becomes weak, unstable, or cleaved when exposed to an external stimuli that is not likely to cause an unintended release of release material 182, such as light of a particular wavelength or sound of a particular frequency that is not typically present during reduced pressure treatment.

A linker material 295 can comprise a variety of molecular compositions depending on the particular embodiment being implemented. An example of a linker material 295 includes, but is not limited to, a benzoin derivative. A linker material 295 can be composed of polymer molecules. The linker polymer molecule can be part of the adhesive itself. A linker material 295 can be hydrophobic, which can maintain the integrity of the seal between a drape 125 and a tissue site 105.

A linker material 295 can comprise a photolabile linker. Photolabile linkers are one or more molecules that weaken or break-down in the presence of electromagnetic energy, such as visible, ultraviolet, or infared light. A photolabile linker, in an absence of electromagnetic energy, can be bound to a release material 182 so as to make the release material 182 inert or immobile. Various types of photolabile linkers can be used depending on the particular embodiment being implemented. A particular photolabile linker can be chosen based on the frequency of light at which the photolabile linker becomes weak, unstable, or is cleaved. Preferably, a photolabile linker becomes weak, unstable, or is cleaved when exposed to electromagnetic radiation having wavelengths that are not substantially detrimental to skin tissue. Such wavelengths can include visible wavelengths, some infrared wavelengths, and some longer ultraviolet wavelengths, as understood in the art.

Examples of photolabile linkers include, but are not limited to, dimethoxybenzoin, dimethylprionic acid, 3,5-dimethoxybenzyl acetate, and 4-(2-chloroproprionyl)phenyl acetic acid. In the example in which the photolabile linkers are dimethoxybenzoin, light having a wavelength of approximately 365 nanometers can be used to weaken or cleave a linker material 295. In the example in which the photolablile linkers are 3,5-dimethoxybenzyl acetate, light having a wavelength of approximately 254 nanometers can be used to weaken or cleave a linker material 295.

A linker material 295 can comprise a light reversible polymer. Examples of a light reversible polymer include, but are not limited to dimerization of coumarin moieties as side chains.

A linker material 295 can comprise a thermo-responsive polymer. Examples of thermo-responsive polymers include, but are not limited to, poly(N-isopropylacrylamide) (NIPAM); poly(ethylene oxide) (PEO); and poly(propylene oxide) (PPO).

A linker material 295 can comprise a shape memory polymer (SMP). Examples of SMPs include, but are not limited to, poly(N,N'-methylenebisacrylamide) and oligo($\epsilon$-caprolactone)dimethylacrylate. A release material 182 can comprise a reversible SMP. Examples of a reversible SMP include, but are not limited to, reversible bonding of epoxy based SMP at 50° C.

A linker material 295 can comprise a pH sensitive polymer. Examples of a pH sensitive polymer include, but are not limited to, poly(methacrylic acids); phospholipids; and silicon-based polysilamine gels.

A linker material 295 can comprise an analyte sensitive polymer. Examples of an analyte sensitive polymer include, but are not limited to, non-enzymatic degradation; insulin/glutathione; and enzymatic sensitive crosslinkers.

A linker material 295 can comprise a photocrosslinker. Examples of a photocrosslinker include, but are not limited to, disialyllacto-N-tetraose (DSLNT) and dental composites.

7. Stimulus 184

In various embodiments, an applied external stimulus 184 facilitates removal of a drape 125 of the system. Various external stimulus 184 can be employed depending on the particular embodiment being implemented. Non-limiting examples of the external stimulus 184 include electromagnetic (e.g., ultraviolet, visible, or infared light), magnetic, sound, pH, pressure (e.g., positive atmospheric pressure, negative atmospheric pressure, shear force, direct force), thermal, moisture, or a substance. External stimulus 184 can also be a substance, compound, liquid, or gas capable of reacting with a release material 182 or a linker material 295 in adhesive layer 477 such that the release material 182 is released.

An external stimulus 184 can disrupt microstructures of the system. An external stimulus 184 can directly or indirectly cause a release material 182 to be released. Disruption of microstructures, disruption of a linker material 295, or release of a release material 182 can facilitate removal of a drape 125 from a tissue site 105. For example, a thermal stimuli can melt a shell of a microstructure or cause material expansion (of the microstructural material or encapsulated payload), thereby rupturing the shell and releasing the contents. Thermal stimulus can be preferred for an acrylic adhesive, solvent release agent, or release agent dependent on crosslinking, or combinations thereof. Thermal stimulus can be direct heat or indirect heat. The use of indirect heat can be less damaging to the surrounding tissue. A magnetic stimuli can take advantage of an oscillating magnetic field to generate heat for an indirect thermal release mechanism of release. For example, where iron oxide in silica (e.g., Magsilica, Evonik) is further encapsulated into a lipid particle, an external oscillating magnetic field can be used to introduce heat into the lipid. Electromagnetic stimuli, such as laser light or high intensity light sources, can be used to induce photooxidative weakening of the microstructure material or to generate heat for an indirect thermal release mechanism of release. Mechanical stimuli can rely on the application of pressure to break a microstructure. But a microstructure must be durable enough to withstand adhesive application and normal use without prematurely rupturing.

In some embodiments, an external stimulus 184 disrupts a microstructure of the system, allowing escape or activation of a release agent. For example, an ultrasonic external stimulus 184 can disrupt release agent-containing micelles located with the adhesive layer 477, resulting in release materials 182 exiting the micelle. As another example, exposure to light as an external stimulus 184 can cause photooxidation of a micelle, allowing escape of a release material 182 contained therein. As another example, exposure to light as an external stimulus 184 can excite a wavelength specific nanorod release agent. As another example, heat, pressure, or the addition of a substance can be used to dissociate a micelle molecules allowing contained release materials 182 to exit the micelle. For example, thermal exposure can expand encapsulated gasses or explosives. As another example, a microstructure can be mechanically ruptured.

In some embodiments, an external stimulus 184 disrupts a linker material 295. As described herein, a disrupted linker material 295 can facilitate removal of a drape 125 from a tissue site 105 through, for example weakening or breaking of a bond between the drape 125, adhesive layer 477, or tissue site 105.

Various embodiments of the drape removal system 405 for facilitating removal of a drape from a tissue site 105 decrease the amount of force necessary to remove a drape. A standard peel test can be used to quantify the amount of force necessary to remove an adhered drape (see e.g., Example 1). The system can decrease the amount of force necessary to remove a drape by at least about 20%. For example, the system can decrease the amount of force necessary to remove a drape by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95%, or by at least about 99%. Preferably, the system can decrease the amount of force necessary to remove a drape by at least about 50%, more preferably by about 75%.

Various embodiments of the drape removal system 405 for facilitating removal of a drape from a tissue site 105 can affect the adhesion strength of the drape prior to exposure to an external stimulus. A standard peel test can be used to quantify the adhesive strength of a drape system (see e.g, Example 1). In some embodiments of the system, the drape has decreased adhesion to the tissue site, as compared to a conventional drape. In some embodiments of the system, the drape has increased adhesion to the tissue site, as compared to a conventional drape. In other words, the presence of intact microstructures, unreleased release agents, or non-cleaved linkers, or a combination thereof, strengthen the adhesion of a drape to a tissue site. For example, a drape of the system (in unreleased configuration) can have more than 100% of the adhesive strength of a convention drape. As another example, a drape of the system (in unreleased configuration) can have at least about 105%, at least about 110%, at least about 120%, at least about 130%, at least about 140%, at least about 150%, at least about 160%, at least about 170%, at least about 180%, at least about 190%, at least about 200%, or more, of the adhesive strength of a convention drape.

One aspect of the invention provides a method for facilitating removal of a drape 125 from a tissue site 105. Various embodiments of the method use any one of the drape removal systems 405 as described above which function as a component of the reduced pressure treatment system 400. The patient or caregiver can determine when to remove the drape 125 from the tissue site 105. When the drape 125 is to be removed, an external stimulus 184 is applied to all or portions of the system 405, such as the adhesive layer 477 containing microstructures or the release agent 482 comprising a release material 182, a release agent comprising a linker material 295, or a combination thereof. Exposure of the system, or portions thereof, to a suitable external stimulus 184 can effect release of a release material 182, cleavage of a linker material 295, or a combination thereof, depending on the embodiment being implemented. A release material 182 or a linker material 295, when activated, released, weakened, or otherwise functionally affected, can alter the adhesion characteristics between the drape 125 and the tissue site 105. The drape 125 can then be removed from the tissue site 105. Such removal process can involve less force, less pain, less trauma, or a combination thereof, as compared to removal of a conventional drape 125.

Referring more specifically to FIG. 5, a flowchart illustrating a process for facilitating removal of a drape 125 from a tissue site 105 is depicted in accordance with an illustrative embodiment of the present invention. The process illustrated in FIG. 5 can be implemented by a user of a reduced pressure treatment system, such as reduced pressure treatment system 400 in FIG. 4.

The process begins by applying a drape 125 to a tissue site 105 (step 505). In this step, either of both of an adhesive layer 477 or a linker material 295 can bind to the tissue site 105. Also in this step, reduced pressure can be applied to the tissue site 105 using the reduced pressure treatment system 400 that includes the drape 125. The process determines whether to remove the drape 125 from the tissue site 105 (step 510). If the process determines not to remove the drape 125 from the tissue site 105, the process returns to step 510.

If the process determines to remove the drape 125 from the tissue site 105, the process applies an external stimulus 184 to the drape 125, including the adhesive layer 477 coupled to the drape 125 (step 515). In this step, a release material 182 can be released or a linker material 295 can be cleaved in accordance with any of the illustrative embodiments described above to facilitate the removal of the drape 125 from the tissue site 105. The process then removes the drape 125 from the tissue site 105 (step 520).

The flowcharts and block diagrams in the different depicted embodiments illustrate the architecture, functionality, and operation of some possible implementations of the apparatus and methods. In some alternative implementations, the function or functions noted in the block can occur out of the order noted in the figures. For example, in some cases, two blocks shown in succession can be executed substantially concurrently, or the blocks can sometimes be executed in the reverse order, depending upon the functionality involved.

Another aspect of the invention is directed toward kits for facilitation of drape removal. Such kits can include the drape removal system of the present invention and, in certain embodiments, instructions for use. Various embodiments of the kit can facilitate performance of the methods described herein, for example, application and removal of a drape 125 system. When supplied as a kit, the different components of the composition can be packaged in a ready to use form or as separate components to be combined just before use. Kit components can include, but are not limited to, dressing, drape 125, manifold, adhesive, adhesive backing, adhesive tape, a release agent, a release material 182, microstructures comprising a release agents, a linker material 295, external stimulus agent, an external energy source, antiseptic swabs, skin preparation swabs, or combinations thereof. Such packaging of the components separately can, if desired, be presented in a pack or dispenser device which can contain one or more applications. The pack may, for example, comprise paper, cloth, metal, or plastic covering. Such packaging of the components separately can also, in certain instances, permit long-term storage without losing activity of the components.

Kits can also include reagents in separate compartments or containers such as, for example, sterile water or saline, bacteriostatic or antibiotic compositions, tissue cleansers, gauze, or other first aid components necessary or useful in wound dressing. The kit can also contain various components for integration of the drape removal system with a reduced pressure treatment system.

In some embodiments, kits can be supplied with instructional materials. Instructions can be printed on paper or other substrate, or can be supplied as an electronic-readable medium, such as a floppy disc, mini-CD-ROM, CD-ROM, DVD-ROM, Zip disc, videotape, audio tape, and the like. Detailed instructions do not have to be physically associated with the kit; instead, a user can be directed to, for example, an Internet web site specified by the manufacturer or distributor of the kit.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention can contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

A 7×7 cm piece of Avery V.A.C.® Therapy Drape was placed on a forearm (specimen 1). The force required to remove the drape 125 was measured by an instron.

A second piece of 7×7 cm drape 125 was placed on the opposite forearm (specimen 2). For this sample, 71.9 mg of jojoba liposomes (Florasomes from Floratech) were placed on the adhesive side of the drape prior to adhering to the forearm. Florasomes liposomes containing about 10% tocopherol (i.e., vitamin E); having a size of about 300 to about 1700 microns; and having an initial melting point of about 50 C. The drape was heated slightly by holding the opposite hand on the dressing for 1 minute. This dressing was attached to the instron and the force required to remove the drape was measured.

Results showed that specimen 1 required a maximum load of 2.44 N to remove. Specimen 2 required a maximum load of 1.48 N to remove. The liposomes slightly reduced maximum load to remove the drape in the absence of heat but such reduction was not significant (data no presented).

According to these results, less load is required to remove the dressing loaded with liposome particles. Thus is providing a showing of a release agent and external stimulus facilitating removal of a drape.

We claim:
1. A system for healing a wound at a tissue site, comprising:
   a drape adapted to cover the wound at the tissue site;
   an adhesive layer having one surface affixed to at least a portion of said drape and an opposite surface adapted to form a bond to the tissue site;
   micelles dispersed within the adhesive layer; and
   release material encapsulated in the micelles and releasable from the micelles into the adhesive layer in response to exposure to light, the release material operable to weaken the bond of the adhesive layer to the tissue site;
   whereby the weakening of the bond of the adhesive layer to the tissue site facilitates the removal of the drape from the tissue site.

2. The system of claim 1 further comprising an adhesive support layer, wherein the adhesive support layer is detachably coupled to the adhesive layer.

3. The system of claim 1 wherein the amount of force required to remove the drape from the tissue site is decreased by at least about 20% of the amount of force required to remove the drape without said release material.

4. The system of claim 1, wherein the release material comprises a sub-ambient $T_g$ material.

5. The system of claim 1, wherein the release material comprises at least one of: polyester resin; adhesion resin; epoxy adhesive; bisphenol glycidylmethacrylate; a surfactant; a silicone particle; a fluorocarbon particle; a thermally degrading adhesive; a Gecko mimicking material; an ultrasonic degraded compound; a thermally reversible adhesive; a mussel adhesive protein; a polymer brush; a solvent induced switching material; a MEMS device; a silicone gel; vitamin E; glycerin; glycerol; stearic acid; glycery stearate; retinyl palmitate; allantoin; limonene, DMSO; IPA; ethyl acetate; tetrahydrofurfuryl acetate; trilaurin; a polyvinylsiloxane microscale pillar; a carbon nanotube; a coated PDMS micropattern; a rippled PDMS film; alkoxylate acrylate; PS; PVP; nitrogen; helium; hydrogen; carbon dioxide; oxygen; active oxygen; carbon dioxide; tartaric acid; bicarbonate; calcium carbonate; citric acid; a chlorogluorocarbon; or a hydrocarbon.

6. The system of claim 1, wherein the release material comprises a plurality of oil particles that, when released on exposure to the external stimulus, weaken a bond between the adhesive layer and the drape or a tissue site wherein the weakened bond decreases the amount of force required to remove the drape from the tissue site.

7. A system for healing a wound at a tissue site, comprising:

a drape adapted to cover the wound at the tissue site;

an adhesive layer having one surface affixed to at least a portion of said drape and an opposite surface adapted to form a bond to the tissue site;

micelles dispersed within the adhesive layer; and release material contained by the micelles and releasable from the micelles into the adhesive layer in response to exposure to light, the release material operable to weaken the bond of the adhesive layer to the tissue site;

whereby the weakening of the bond of the adhesive layer to the tissue site facilitates the removal of the drape from the tissue site, and wherein the micelles comprise at least one of: polyethylene glycol, pluronics, phospholipids, lecithin, casein, a non-ionic surfactant; or a combination thereof.

* * * * *